(12) United States Patent
Biedermann et al.

(10) Patent No.: US 8,771,357 B2
(45) Date of Patent: Jul. 8, 2014

(54) FLEXIBLE SPACE HOLDER

(75) Inventors: Lutz Biedermann, VS-Villingen (DE);
Jürgen Harms, Karlsruhe (DE);
Wilfried Matthis, Weisweil (DE)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 1085 days.

(21) Appl. No.: 11/121,888

(22) Filed: May 4, 2005

(65) Prior Publication Data
US 2005/0267471 A1    Dec. 1, 2005

Related U.S. Application Data

(60) Provisional application No. 60/567,989, filed on May 4, 2004.

(30) Foreign Application Priority Data

May 4, 2004  (DE) .......................... 10 2004 021 861

(51) Int. Cl.
*A61F 2/44* (2006.01)

(52) U.S. Cl.
USPC .................................... 623/17.16; 623/17.11

(58) Field of Classification Search
USPC .............................. 623/17.13–17.16; 403/229
See application file for complete search history.

(56) References Cited

U.S. PATENT DOCUMENTS

| | | | |
|---|---|---|---|
| 1,950,448 A * | 3/1934 | Heisterkamp | 464/57 |
| 4,820,305 A | 4/1989 | Harms et al. | |
| 4,846,839 A * | 7/1989 | Noiles | 623/23.46 |
| 4,960,420 A * | 10/1990 | Goble et al. | 606/232 |
| 5,002,576 A * | 3/1991 | Fuhrmann et al. | 623/17.15 |
| 5,171,281 A * | 12/1992 | Parsons et al. | 623/17.15 |
| 5,197,488 A * | 3/1993 | Kovacevic | 600/595 |
| 5,306,307 A * | 4/1994 | Senter et al. | 623/17.16 |
| 5,306,310 A * | 4/1994 | Siebels | 623/17.13 |
| 5,320,644 A | 6/1994 | Baumgartner | |
| 5,370,697 A | 12/1994 | Baumgartner | 623/17 |
| 5,375,823 A | 12/1994 | Navas | |
| 5,423,816 A * | 6/1995 | Lin | 606/247 |
| 5,423,817 A | 6/1995 | Lin | 606/61 |
| 5,458,642 A | 10/1995 | Beer et al. | |

(Continued)

FOREIGN PATENT DOCUMENTS

| | | | |
|---|---|---|---|
| DE | 36 37 314 A1 | 5/1988 | |
| DE | 43 23 034 C1 | 7/1994 | |

(Continued)

OTHER PUBLICATIONS

German Search Report for application No. 10 2006 003 374.4, 3 sheets.

(Continued)

*Primary Examiner* — Eduardo C Robert
*Assistant Examiner* — Julianna N Harvey
(74) *Attorney, Agent, or Firm* — Christie, Parker & Hale, LLP (57) ABSTRACT

The present invention refers to a flexible space holder for temporary or permanent introdution into a human or animal body of at least one biocompatible, rigid material having a tube-like body (1), with one or more flexible areas being formed by material recesses mare provided for.

26 Claims, 5 Drawing Sheets

(56) References Cited

U.S. PATENT DOCUMENTS

| | | | |
|---|---|---|---|
| 5,571,192 A | 11/1996 | Schönhöffer | |
| 5,609,637 A | 3/1997 | Biedermann et al. | |
| 5,672,175 A | 9/1997 | Martin | |
| 5,674,294 A | 10/1997 | Bainville et al. | |
| 5,702,449 A | 12/1997 | McKay | |
| 5,702,451 A | 12/1997 | Biedermann et al. | |
| 5,702,453 A | 12/1997 | Rabbe et al. | |
| 5,702,455 A | 12/1997 | Saggar | |
| 5,755,798 A | 5/1998 | Papavero et al. | |
| 5,782,832 A | 7/1998 | Larsen et al. | 606/61 |
| 5,897,556 A | 4/1999 | Drewry et al. | |
| 5,904,719 A * | 5/1999 | Errico et al. | 623/17.16 |
| 5,989,290 A * | 11/1999 | Biedermann et al. | 623/17.11 |
| 6,015,436 A | 1/2000 | Schönhöffer | |
| 6,039,762 A | 3/2000 | McKay | |
| 6,086,613 A * | 7/2000 | Camino et al. | 623/17.16 |
| 6,113,638 A | 9/2000 | Williams et al. | |
| 6,143,032 A | 11/2000 | Schafer et al. | |
| 6,176,882 B1 | 1/2001 | Biedermann et al. | |
| 6,190,413 B1 | 2/2001 | Sutcliffe | |
| 6,193,755 B1 | 2/2001 | Metz-Stavenhagen et al. | |
| 6,193,756 B1 | 2/2001 | Studer et al. | |
| 6,200,348 B1 | 3/2001 | Biedermann et al. | |
| 6,296,664 B1 * | 10/2001 | Middleton | 623/17.15 |
| 6,299,644 B1 | 10/2001 | Vanderschot | |
| 6,395,035 B2 | 5/2002 | Bresina et al. | |
| 6,402,750 B1 | 6/2002 | Atkinson et al. | |
| 6,440,169 B1 | 8/2002 | Elberg et al. | |
| 6,454,805 B1 | 9/2002 | Baccelli et al. | |
| 6,579,321 B1 * | 6/2003 | Gordon et al. | 623/17.16 |
| 6,582,468 B1 | 6/2003 | Gauchet | |
| 6,610,090 B1 | 8/2003 | Böhm et al. | |
| 6,770,094 B2 | 8/2004 | Fehling et al. | |
| 6,866,682 B1 | 3/2005 | An et al. | |
| 6,964,686 B2 | 11/2005 | Gordon | |
| 7,166,131 B2 | 1/2007 | Studer et al. | |
| 7,179,295 B2 | 2/2007 | Kovacevic | |
| 7,651,515 B2 | 1/2010 | Mack et al. | |
| 2001/0016774 A1 | 8/2001 | Bresina et al. | |
| 2002/0035366 A1 | 3/2002 | Walder et al. | |
| 2002/0035400 A1 * | 3/2002 | Bryan et al. | 623/17.15 |
| 2002/0082696 A1 | 6/2002 | Harms et al. | |
| 2002/0143399 A1 | 10/2002 | Sutcliffe | |
| 2002/0161444 A1 | 10/2002 | Choi | |
| 2003/0009223 A1 | 1/2003 | Fehling et al. | |
| 2003/0109880 A1 | 6/2003 | Shirado et al. | |
| 2003/0181980 A1 | 9/2003 | Berry et al. | |
| 2003/0191470 A1 | 10/2003 | Ritland | |
| 2003/0191531 A1 | 10/2003 | Berry et al. | |
| 2003/0220643 A1 | 11/2003 | Ferree | |
| 2004/0002761 A1 | 1/2004 | Rogers et al. | |
| 2004/0006390 A1 * | 1/2004 | Duarte | 623/17.11 |
| 2004/0049271 A1 | 3/2004 | Biedermann et al. | |
| 2004/0143330 A1 | 7/2004 | Sazy | |
| 2004/0172129 A1 | 9/2004 | Schafer et al. | |
| 2004/0176172 A1 | 9/2004 | Berg | |
| 2005/0043804 A1 | 2/2005 | Gordon et al. | 623/17.16 |
| 2005/0056979 A1 | 3/2005 | Studer et al. | |
| 2005/0065514 A1 | 3/2005 | Studer | |
| 2005/0085909 A1 * | 4/2005 | Eisermann | 623/17.11 |
| 2005/0203519 A1 | 9/2005 | Harms et al. | |
| 2006/0058879 A1 | 3/2006 | Metz-Stavenhagen | |
| 2006/0129147 A1 | 6/2006 | Biedermann et al. | |
| 2006/0241760 A1 | 10/2006 | Randall et al. | |
| 2007/0198088 A1 * | 8/2007 | Biedermann et al. | 623/17.11 |
| 2011/0040385 A1 | 2/2011 | Biedermann et al. | |

FOREIGN PATENT DOCUMENTS

| | | | |
|---|---|---|---|
| DE | 44 09 392 A1 | 9/1995 | |
| DE | 44 23 257 A1 | 1/1996 | |
| DE | 195 04 867 C1 | 2/1996 | |
| DE | 195 09 317 A1 | 9/1996 | |
| DE | 195 19 101 A1 | 11/1996 | |
| DE | 196 22 827 A1 | 12/1997 | |
| DE | 198 04 022 A1 | 6/1999 | |
| DE | 198 03 700 A1 | 8/1999 | |
| DE | 198 16 782 A1 | 10/1999 | |
| DE | 298 24 158 U1 | 10/2000 | |
| DE | 200 15 265 U1 | 1/2001 | |
| DE | 199 44 681 A1 | 3/2001 | |
| DE | 100 56 977 C2 | 6/2002 | A61F 2/44 |
| DE | 100 65 398 A1 | 7/2002 | |
| DE | 101 16 412 C1 | 1/2003 | |
| DE | 202 13 013 U1 | 1/2003 | |
| DE | 102 10 214 A1 | 9/2003 | |
| DE | 697 19 431 T2 | 9/2003 | |
| DE | 698 13 807 T2 | 3/2004 | |
| DE | 102 42 331 A1 | 4/2004 | |
| DE | 103 27 358 A1 | 1/2005 | |
| DE | 698 22 508 T2 | 1/2005 | |
| DE | 600 15 879 T2 | 3/2005 | |
| DE | 699 16 261 T1 | 4/2005 | |
| DE | 699 16 261 T2 | 4/2005 | |
| DE | 10 2004 011 685 A1 | 9/2005 | |
| DE | 10 2004 018 621 B4 | 6/2006 | |
| EP | 0 268 115 A1 | 5/1988 | |
| EP | 0 346 129 A1 | 12/1989 | A61F 2/44 |
| EP | 0 529 275 A2 | 3/1993 | A61F 2/44 |
| EP | 0 677 277 A2 | 10/1995 | |
| EP | 0 770 367 A1 | 5/1997 | |
| EP | 0 797 418 B1 | 10/1997 | |
| EP | 0 836 454 B1 | 4/1998 | |
| EP | 0 904 751 A1 | 3/1999 | |
| EP | 0 669 109 B1 | 5/1999 | |
| EP | 0 950 389 A2 | 10/1999 | A61F 2/44 |
| EP | 0 950 389 A3 | 10/1999 | A61F 2/44 |
| EP | 0 959 389 A1 | 11/1999 | G03F 7/004 |
| EP | 0 988 003 B1 | 3/2000 | |
| EP | 1 188 416 A1 | 3/2002 | |
| EP | 1 236 451 A1 | 9/2002 | |
| EP | 1 273 276 A2 | 1/2003 | A61F 2/44 |
| EP | 1 273 278 A2 | 1/2003 | A61F 9/00 |
| FR | 2 634 371 | 1/1990 | |
| FR | 2 717 370 | 9/1995 | |
| FR | 2 734 148 | 11/1996 | |
| FR | 2 774 581 | 8/1999 | |
| JP | 63-177851 A | 7/1988 | |
| JP | 5-277141 | 10/1993 | |
| JP | 7-8504 | 1/1995 | |
| JP | 7-255741 | 10/1995 | |
| JP | 8-98850 | 4/1996 | |
| JP | 08-238266 | 9/1996 | |
| JP | 2561401 B2 | 12/1996 | |
| JP | 2769926 | 4/1998 | |
| JP | 11-505736 | 5/1999 | |
| JP | 2000-513263 | 10/2000 | |
| JP | 2001-507243 A | 6/2001 | |
| JP | 2001-526083 A | 12/2001 | |
| JP | 2002-502299 A | 1/2002 | |
| JP | 2002-518090 | 6/2002 | |
| JP | 2002-524140 | 8/2002 | |
| JP | 2002-527196 A | 8/2002 | |
| JP | 2002-532140 A | 10/2002 | |
| JP | 2003-623 A | 1/2003 | |
| JP | 2003-24353 | 1/2003 | |
| JP | 2003-38505 A | 2/2003 | |
| JP | 2003-518409 | 6/2003 | |
| WO | WO 95/19153 | 7/1995 | A61F 2/44 |
| WO | WO 98/56319 | 12/1998 | |
| WO | WO 99/32055 | 7/1999 | |
| WO | WO 99/65425 | 12/1999 | A61F 2/44 |
| WO | WO 02/17825 A2 | 3/2002 | A61F 2/44 |
| WO | WO 02/28297 A1 | 4/2002 | |
| WO | WO 02/085261 A1 | 10/2002 | A61F 2/44 |
| WO | WO 03/013399 A1 | 2/2003 | |
| WO | WO 03/047441 A1 | 6/2003 | |
| WO | WO 03/047442 A1 | 6/2003 | |
| WO | WO 2004/016217 A2 | 2/2004 | |

(56) References Cited

FOREIGN PATENT DOCUMENTS

| WO | WO 2004/037131 A1 | 5/2004 |
|----|-------------------|--------|
| WO | WO 2004/105577 A2 | 12/2004 |

OTHER PUBLICATIONS

Application No. PCT/CH02/00180 dated Dec. 7, 2011, 20 pages.
International Search Report for Application No. PCT/EP2004/011782, dated May 18, 2005, 7 sheets.
European Search Report for Application No. EP 0500 9856, dated Aug. 31, 2005, 3 sheets.
Office action dated May 21, 2009 for U.S. Appl. No. 10/575,699, 9 sheets.
Final Rejection dated Feb. 22, 2010 for U.S. Appl. No. 10/575,699, 5 sheets.
Office action dated May 18, 2010 for U.S. Appl. No. 10/575,699, 9 sheets.
Office action dated Jun. 1, 2010 for U.S. Appl. No. 11/588,687, 9 sheets.
Final Rejection dated Jan. 12, 2011 for U.S. Appl. No. 11/588,687, 10 sheets.
Search Report of priority application DE 10 2004 021 861.7, Oct. 8, 2005, 1 sheet.
German Search Report for application No. 10 2006 003 374.4, 3 sheets, 2007.
Korean Search Report for application No. PCT/KR2005/000651, dated Jul. 12, 2005, 3 sheets.

\* cited by examiner

FLEXIBLE SPACE HOLDER

REFERENCE TO EARLIER FILED APPLICATIONS

The present invention claims the benefit of the filing date under 35 U.S.C. §119(e) of Provisional U.S. Patent Application Ser. No. 60/567,989, filed May 4, 2004, which is hereby incorporated by reference. The present application also claims foreign priority benefits pursuant to 35 U.S.C. §119 (a-d) for German Patent Application No. 10 2004 021 861.7 filed May 4, 2004 in Germany.

BACKGROUND

The invention relates to a flexible space holder. The flexible space holder can be inserted into a human or animal on a temporary or permanent basis.

In modern medicine, many defects in the human or animal body can be compensated or minimized by the use of implants. For example, space holders for vertebrae or intervertebral discs are known to be used as replacements for a vertebral body or an intervertebral disc.

It is important to use materials which are compatible with the human or animal organism, so that the implant is not rejected or does not disintegrate upon being implanted. Accordingly, the choice of materials for implants is important and somewhat restricted.

In addition, it is advantageous to form simple space holders from as few parts as possible. The more parts the space holder is made from, the harder to implant and the greater the possibility of malfunction at the connection site. Therefore, preferably implants are formed from as few parts as possible.

Despite these issues, space holders must fulfill several different functions, making it desirable to use different materials and/or several parts in forming the space holders. For example, it is desirable for spacer holders not only to fill the space and hold the vertebrae at a certain distance from each other, but also to facilitate a certain degree of movement of the vertebrae towards each other, i.e. enabling movement and articulation within certain narrow limits.

DE 10056977 C2 describes a space holder with a bellows-shaped piece of tubing extending in the longitudinal direction of the implant between support elements which abut the vertebral bodies. The bellows-shaped piece of tubing is made from a tightly woven or knit textile material. This space holder, however, has the disadvantage described above, in that several different types of materials are used and are then connected to each other. In view of the materials and construction, there is an increased risk of possible malfunction of the space holder.

The object of the present invention is therefore to provide flexible space holders which are made of the fewest possible parts, yet which provide a certain degree of flexibility and mobility within the implant or region wherein the implant is implanted. Preferably, the space holder is made of one piece of material or a few pieces that are easily interconnected, so that the flexible space holder can provide the desired degree of flexibility and mobility. In addition, the flexible space holders of the instant invention are easy to manufacture and implant, are safe in operation, and have a long lifetime and diverse application possibilities.

In the prior art, space holders with the desired mobility or elasticity are obtained using various parts connected together. In addition, the individual parts of these prior art space holders generally are made of different materials that are connected together to form the space holder. This invention, however, in one embodiment, provides for a flexible space holder made from one type of material which imparts the desired flexibility and mobility to the flexible space holder, by placing recesses in the actual flexible space holder itself.

BRIEF SUMMARY

A flexible space holder for vertebrae and/or intervertebral discs with space-holder and weight-transfer function for temporary or permanent introduction into a human or animal body of at least one biocompatible material comprising a tube-like body with a recess extending along its circumference in order to locally reduce the rigidity of the tube-like body, said tube-like body having a first end and a second end and means for connecting said flexible space holder to adjacent body parts at said first end and second end of said tube-like body.

A flexible space holder for vertebrae and/or intervertebral discs with space-holder and weight-transfer function of at least one biocompatible material having a tube-like body, comprising at least one recess to locally reduce the rigidity of the space holder and means for connecting said flexible space holder to adjacent body parts.

A flexible space holder for vertebrae and/or intervertebral discs with space-holder and weight-transfer function comprising a tube-like body which is elastically extendable or compressible by about 0.5 to about 20%.

A flexible space holder for vertebrae and/or intervertebral discs with space-holder and weight-transfer function comprising a tube-like body with a recess surrounded by an elastic sleeve.

A space holder for vertebrae and/or intervertebral discs with space-holder and weight-transfer function comprising a tube-like body with a recess with an replaceable elastic core inserted into the tube-like body.

The foregoing paragraphs have been provided by way of general introduction, and are not intended to limit the scope of the following claims. The presently preferred embodiments, together with further advantages, will be best understood by reference to the following detailed description taken in conjunction with the accompanying drawings.

BRIEF DESCRIPTION OF THE DRAWINGS

FIGS. 4 (a) and (c) are exploded three-dimensional views of a second embodiment of the flexible space holder;

FIG. 4 (b) is a three-dimensional sectional view of the second embodiment of the flexible space holder;

FIGS. 5 (a)-(c) are three-dimensional views of a third embodiment of the flexible space holder.

DETAILED DESCRIPTION OF THE DRAWINGS AND PRESENTLY PREFERRED EMBODIMENTS

Various embodiments of the invention are illustrated in FIGS. 1 to 5 and described herein. Elements of the various embodiments that are substantially identical will be referred to with the reference numerals.

The flexible space holders according to this invention have a cylindrical tube-like body. The tube-like body has connection elements provided on each end of said tube-like body. In addition, the tube-like body has recess(es) along the circumference of the tube-like body which are responsible for the flexibility of the flexible space holder. The recess(es) can be placed anywhere along the tube-like body provided that the recess reduces the rigidity of the body. Preferably, the recess(es) are centered along the length of the tube-like body. Alternatively, the recess(es) can be off-centered.

The connection elements of the flexible space holders preferably have corresponding means of connecting the flexible space holder to adjacent body parts, such as vertebrae or bone. These connection elements can be in any form provided that they are able to connect to the adjacent body part. The exact composition and configuration of the connection elements are well within the purview of one of ordinary skill in the art. For example, the connection elements can be in the form of hook-like projections on the ends and/or recesses, grooves and openings on the surface of the connection element so that the flexible space holder may grow into, knit with and become part of the tissue into which it is implanted. Because the connection elements knit or mesh completely with the adjacent body parts, such as the vertebrae, they do not contribute to the flexibility or mobility of the flexible space holder. However, the grooves or recesses of the connection elements must not be confused with the recesses (which will be described in further detail below) found on the tube-like body which impart flexibility and mobility to the flexible space holder in the tube-like body part.

Preferably, the flexible space holder is stable and stiff, especially in view of the conditions in which it is used. A rigid, preferably flexible rigid material, is used for the flexible space holder. Materials such as titanium, titanium alloys, plastics and the like can be used to form the flexible space holder. Generally, all biocompatible materials are candidates so long as they do not cause rejection reactions or show any disintegration when placed in the body. Other examples of biocompatible materials to form said flexible space holder include stainless steel, nickel-titanium alloys, nitinol, chrome alloy, cobalt chrome alloys, shape memory alloys, materials with super elastic properties, carbon reinforced composites, silicone, polyurethane, polyester, polyether, polyalkene, polyethylene, polyamide, poly(vinyl) fluoride, polyetheretherketone (PEEK), polytetrafluoroethylene (PTFE) and shape memory materials or alloys, such as nickel titanium or nitinol.

The recesses in the tube-like body can preferably be provided in the form of groove-shaped recesses or open apertures in the walls of the tube-like body as described above. The shape, number and arrangement of the recesses can be adjusted from case to case depending upon the load requirements as will be appreciated by those of ordinary skill in the art.

In order to satisfy the diverse functions of the flexible space holder, including weight transfer, the recess(es) can be provided in the form of a helix running around the wall of the tube-like body. The use of the helical shaped recess is especially advantageous in this case because free spaces are present between adjacent fillets of the helical shaped recess. Aside from being easier to manufacture and the associated larger choice of material that could be used, this embodiment also has the advantage of achieving greater flexibility than the prior art space holders. Although a helix is described, it will be appreciated by those skilled in the art that other shaped recesses can be used to achieve the desired flexibility and mobility in the tube-like body.

Figure 6:
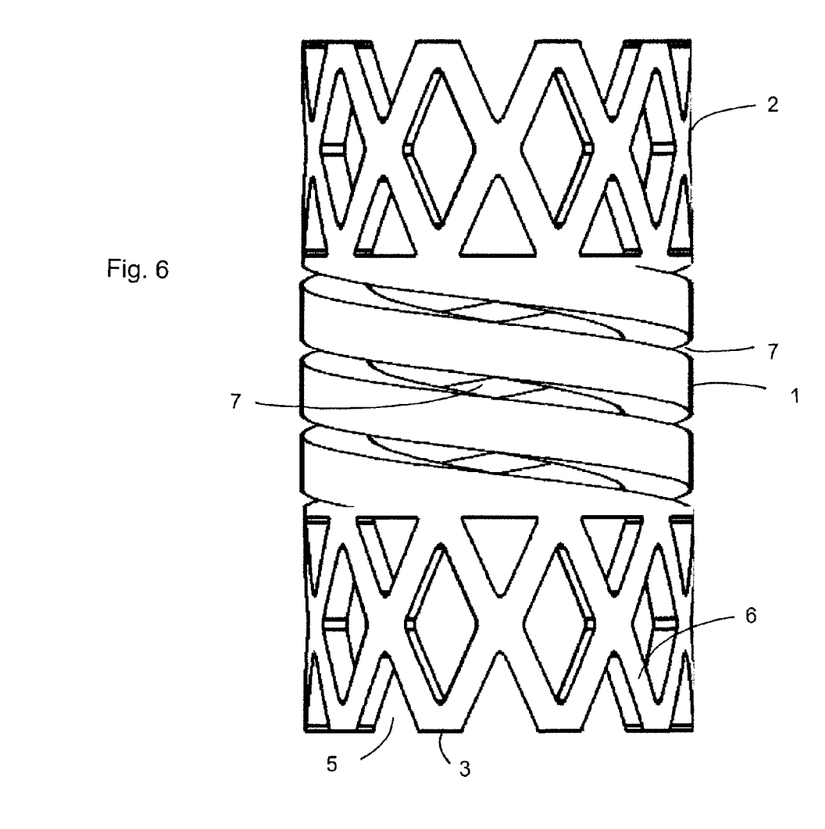
FIG. 6 is a three-dimensional view of a space holder for vertebrae or intervertebral discs according to a fourth embodiment.

In another embodiment, as shown in FIG. 6, two recesses can be provided in the wall of the tube-like body in the form of a twin-track or a two-flight helix. In this way, two helical shaped recesses can be arranged inside each other. If the area of the helix-shaped recess has the same height, two helix-shaped recesses of double pitch can be provided instead of one helix-shaped recess of a low pitch.

In order to further refine the mobility and flexibility of the flexible space holder, an elastic sleeve can be placed around the tube-like body. Alternatively, an elastic core can be inserted into the tube-like body. Such an elastic core or elastic sleeve, comprising, preferably of an elastomer, offers the advantage that it allows the elasticity or rigidity of the tube-like body or space holder to be precisely adjusted by choosing the material of the elastic core or elastic sleeve so that the elastic core or elastic sleeve has the desired elasticity. In addition to elastomers, other engineered polymers can be used to form the elastic sleeve or elastic core provided that they have the desired properties.

The connection elements or the means for connecting the tube-like body to adjacent body parts may be arranged either integrally with the tube-like body or detachably on the ends of the tube-like body. An example of a detachable connector includes end plates that can be screwed onto the ends of the tube-like body. It will be appreciated by those of ordinary skill in the art that other types of connections can be used.

Detachable end plates or end plates connected integrally with the tube-like body are preferably used when at least one sleeve of elastic material is arranged around the tube-like body with the recesses, or at least one elastic core is provided within the tube-like body for the purpose of achieving the desired elasticity or mobility.

Through the use of modular-like arrangement of tube-like body with corresponding recesses, and core and/or sleeve, and the use of different components of different rigidity, the damping ability of the flexible space holder can be defined. The combination of a flexible space holder with recesses as well as a space holder having parts made of a flexible material, enables the flexible space holder of the instant invention to have the desired flexibility and mobility and the specification of each particular element of the flexible space holder is well within the skill of one in the art. With this construction, it is possible to realize compression, torsion and/or expansion zones in a simple and reliable manner, especially in an integral flexible space holder.

To alter the characteristics of the flexible space holder, the composition of the components can simply be changed. For example, a core of different rigidity or a different sleeve can be used in conjunction with the flexible space holder comprising a tube-like body with recesses. Although it is conceivable that a sleeve and a core can be used simultaneously together with a flexible tube-like body, for the sake of simplicity it will usually only be a combination of tube-like body and core or tube-like body and sleeve. In this regard, the sleeve also offers the further advantage of protecting the tube-like body with the preferably helix-shaped recesses against external influences, whereas, the tube-like body actually protects the core when the core is used.

Both core and sleeve can advantageously be held by the arrangement of end plates on the ends of the tube-like body, with, in the case of the arrangement of a sleeve, the end plates projecting preferably beyond the tube-like body and thus having a larger diameter than the tube-like body. The end plates can at least partly, that is on one side, be connected integrally with the tube-like body, such that a beaker-like shape is obtained. In addition, the end plates can be connected detachably either on one side or on two sides to the tube-like body, for example via a screw or thread connection. In this regard, the outer thread can be provided both on the end plate and on the tube-like body.

Preferably, the flexible space holder or the tube-like body with the material recesses for obtaining flexibility and mobility is extensible or compressible in its longitudinal direction along the space holder longitudinal axis by 0.5 to 20%, especially 1 to 15%, and bendable about a radial axis perpendicular to the longitudinal axis of the space holder, so that tube-like body can be pivoted by approximately 0.5 to 10, especially 1 to 6 degrees with reference to the longitudinal axis. In addition, in a preferred embodiment, a torsional movement of 0.5° to 2.5° about the longitudinal axis is possible.

Figure 1:
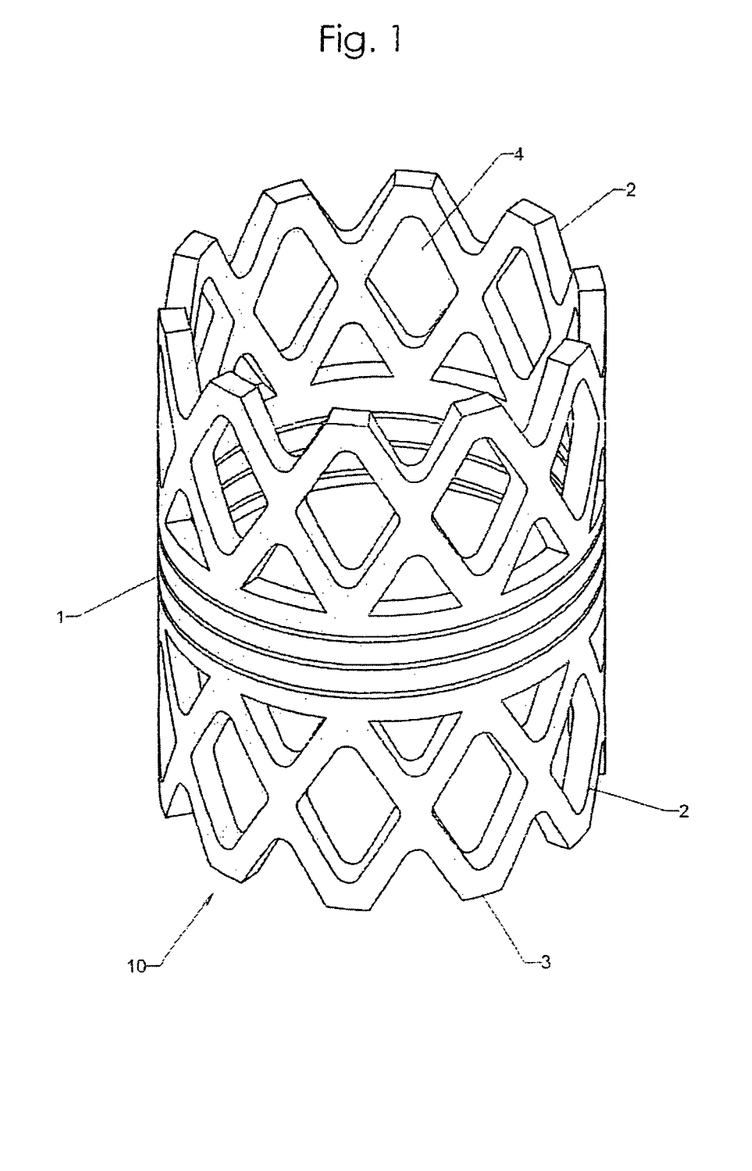
FIG. 1 is a three-dimensional view of a space holder for vertebrae or intervertebral discs.

FIG. 1 is a three-dimensional view of a first embodiment of the flexible space holder, in accordance with the invention. Flexible space holder 10 has a tube-like body 1 and two connection elements 2 provided at each end of the tube-like body 1 for connecting the space holder 10 to the adjacent body parts, e.g. bones or cartilage in, for example, the human body.

Connection elements 2, which are arranged at the ends of the tube-like body 1, have identical shapes in the embodiment shown, but each may also have a different shape. In the embodiment shown, the connection elements 2 are integral to the tube-like body have serrations 3 on each free end of their ends that can engage with the adjacent body tissue at the site of implantation. Serrations 3 are formed by triangular recesses 5 on both ends of space holder 10, such that trapezoidal serrations 3 are formed that can engage with and cling on to adjacent body tissue.

Figure 2:
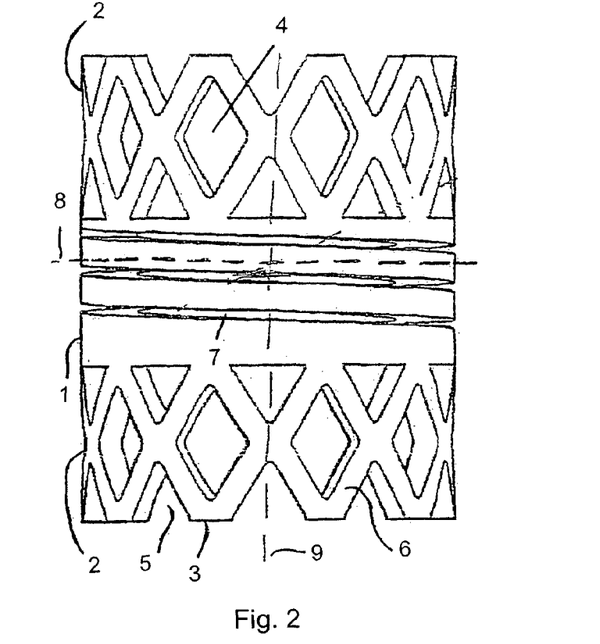
FIG. 2 is a lateral view of the space holder shown in FIG. 1.

In addition, connection elements 2 may have diamond-shaped cavities 4 as shown in FIG. 2, that are adjacent to each other around the entire circumference of cylinder jacket surface of connection elements 2. As a result, the respective connection element is formed by a large number of diamond-shaped interconnected fillets 6, with the tips of the diamonds formed by fillets 6 cut-off so that trapezoidal serrations 3 are formed.

Figure 3:
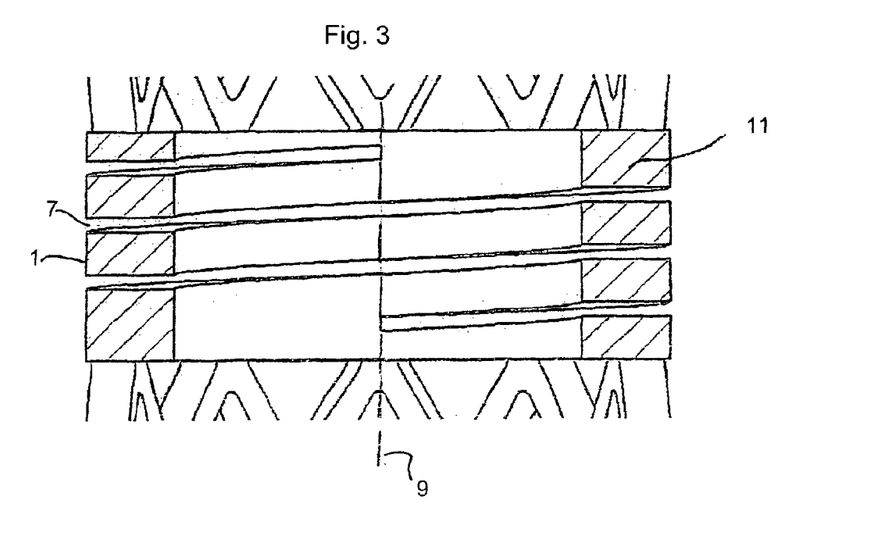
FIG. 3 is a detailed lateral view of the space holder shown in FIGS. 1 and 2.

Tube-like body 1 between connection elements 2 on each end of the tube-like body includes, in the embodiment shown, a helix-shaped recess 7 in the cylinder itself, around the circumference of the tube-like body. With this construction, the wall 11 of the flexible space holder as seen in FIG. 3 itself assumes a helix shape.

Flexible space holder 10 is formed overall as a hollow cylinder, tube-like body 1 with recesses 7 formed in the material of the tube-like body, around the circumference of the body between the connection elements 2. This design provides for a moveable elastic area, even if the flexible space holder 10, itself is formed from an essentially stiff or rigid material, such as titanium or a titanium alloy. Through the use of recesses 7 in the tube-like body itself, the flexible space holder 10 receives a design-related elasticity in the region of the tube-like body 1, which makes it possible to dispense with provision of a separate elastic material in this area to obtain elasticity or mobility of the device. With this design, a flexible space holder can be made from a single piece of material.

Moreover, by using the helix-shaped recesses 7, the tube-like body 1 is extendable and compressible along longitudinal axis 9 of flexible space holder 10 and bendable about a rotary axis perpendicular to longitudinal axis 9, which for example is illustrated by axis 8 in FIG. 2. In this particular embodiment, the helix shape of the recess 7 enables balanced elasticity or mobility in the most directions that the vertebrae would move. Naturally, however, it will be appreciated by those skilled in the art that other shapes of recesses and a different number and arrangement of these recesses are possible. Furthermore, various different shapes can be used to adapt to individual cases or load profiles.

Figure 4:
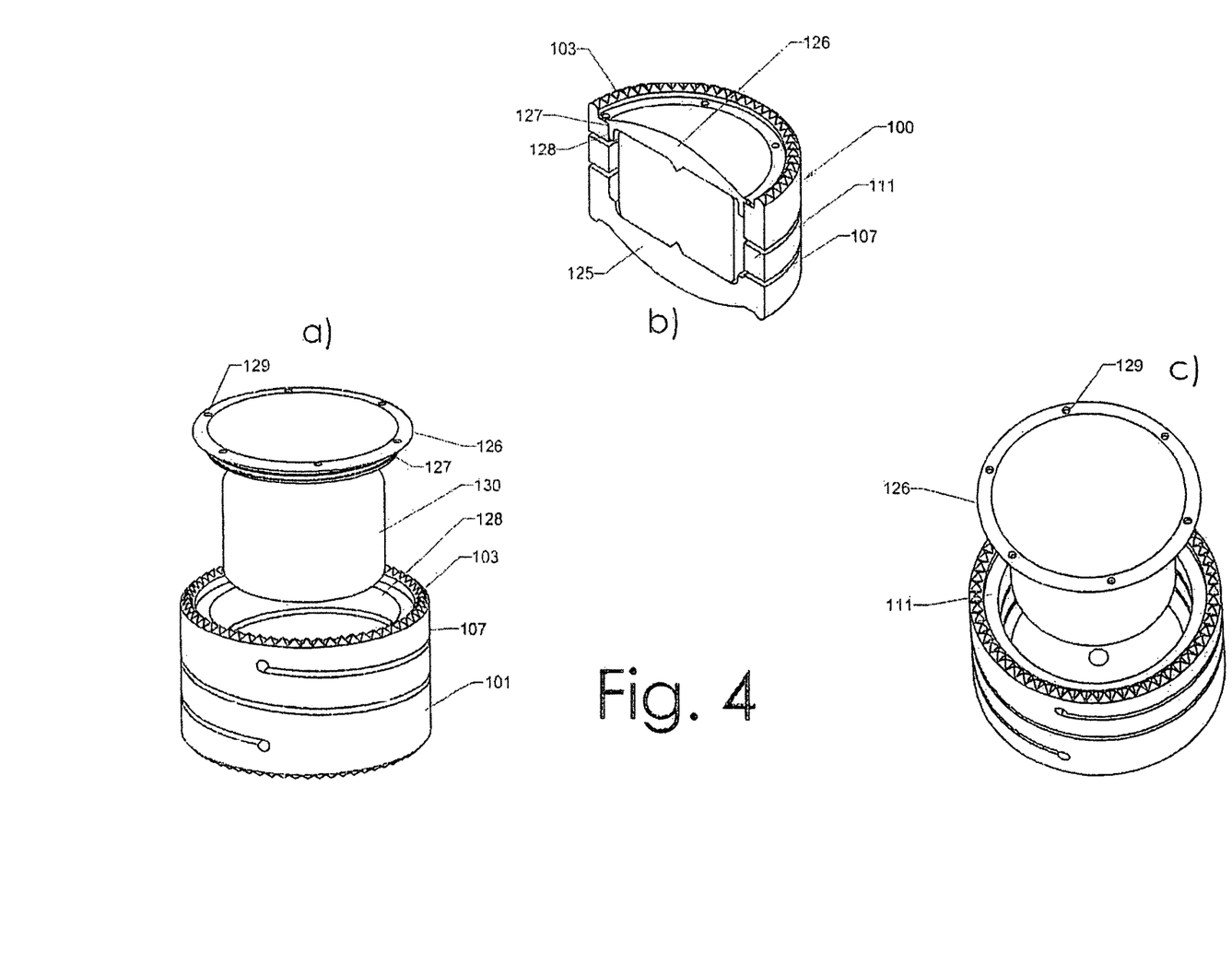

FIG. 4, in sub-figures (a) and (c), shows two different exploded three-dimensional views of a second embodiment of a flexible space holder 100 with a tube-like body 101. A sectional view of a second embodiment is shown in FIG. 4(b). In this second embodiment, the tube-like body is sealed on the lower side by an end plate 125 connected integrally with the tube-like body 101, so that a beaker-like shape results.

As illustrated in this second embodiment, tube-like body 101 has in its walls 111 a helix-shaped recess 107 that imparts desired flexibility in accordance with the invention to the tube-like body 101. To be able to further adjust the stiffness of the flexible space holder 100, 101 a replaceable core element 130 of an elastomeric material is inserted into the tube-like body. The replaceable core element 130 is held on the lower side by end plate 125 and on the upper side by end plate 126 in tube-like body 101. It will be appreciated by those skilled in the art that the rigidity and material used for the replaceable core element will impact the elasticity and rigidity of the flexible space holder. End plate 126 on the upper side of the flexible space holder has an external thread 127, so that it can be screwed into internal thread 128 of tube-like body 101 located on the upper end in the inside of tube-like body 101 in this embodiment. End plate 126 also has a shoulder which lies tightly against wall 111. Serrations 103 are provided all around the end of wall 111 and project over end plates 125 and 126 and can engage with adjacent tissue in order to hold the space holder firmly in position.

End plate 126 also has engagement openings 129 so that end plate 126 can be screwed into the tube-like body 101. End plates 125 and 126 may additionally be roughened or coated by a bio-active material to assist with engagement to adjacent body tissue. Examples of suitable bio-active materials include, but are not limited to, ceramics such as hydroxypatite coatings, biopolymers such as chitosan, and bio-active glass. The choice of a bio-active materials is well within the purview of one of ordinary skill in the art.

Figure 5:
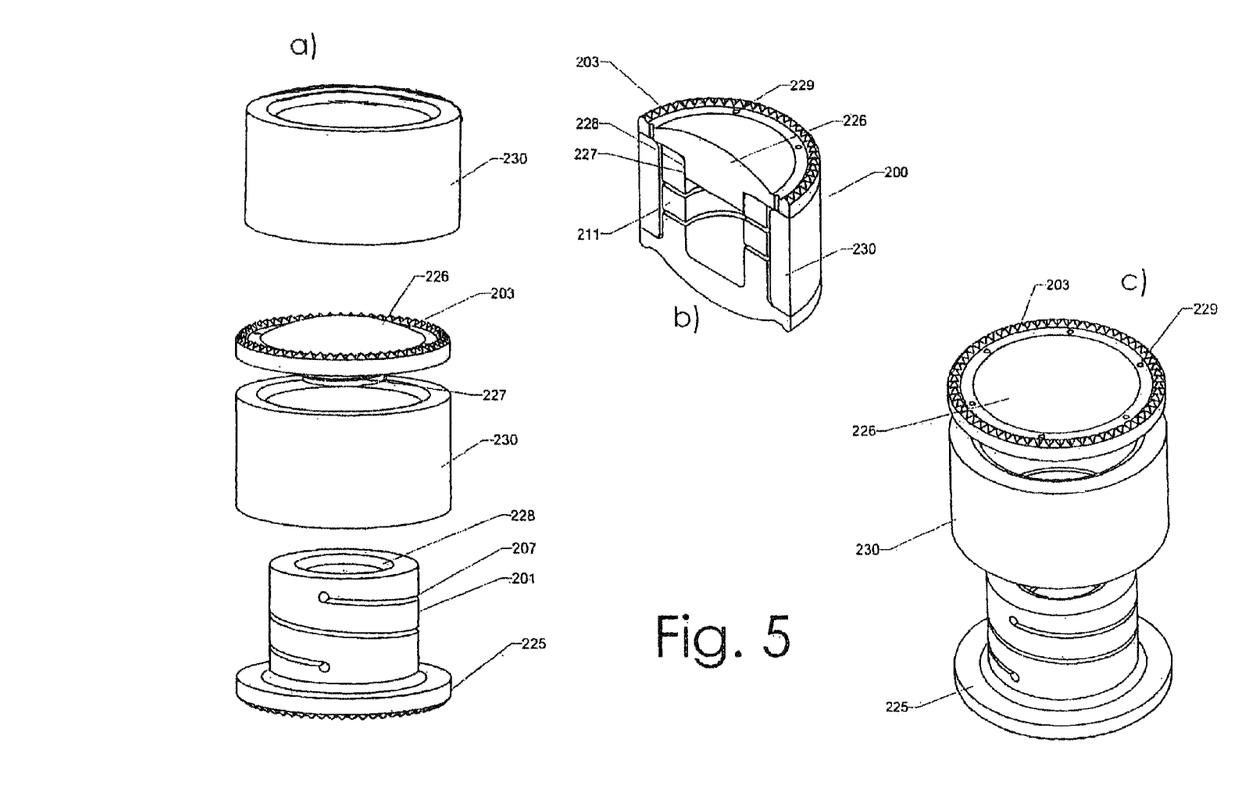

A third embodiment of a flexible space holder is shown in FIG. 5, sub-figures (a)-(c). Sub-figures (a) and (c) represent an exploded three-dimensional view of the flexible space holder, while sub-figure (b) shows a three-dimensional sectional view of the flexible space holder.

The embodiment of FIG. 5 includes a helix-shaped recess 207 in body wall 211 of tube-like body 201. The lower side of the tube-like body 201 is closed by an integrally arranged end plate 225, so that a beaker-like shape described above results. The end plate 225 is formed so that it has a larger outer diameter than tube-like body 201, in which the helix-shaped recess 207 is arranged in the material of the tube-like body 201, so a shoulder is created that forms a receptacle for a tube-like sleeve 230 of elastomeric material. Elastic sleeve 230 is pushed over tube-like body 201 so that the tube-like body is completely surrounded by the sleeve. An end plate 226 is screwed onto tube-like body 201 at its upper end by means of a thread connection. In this regard, the outer thread 227 of end plate 226 engages with internal thread 228 of tube-like body 201, so that sleeve 230 is held firm between end plates 225 and 226. Sleeve 230 also serves to adjust the overall rigidity of the flexible sleeve device, in that simply exchanging sleeve 230, in a manner similar to exchanging core 130, described with respect to the embodiment of FIG. 4, makes it possible to simply vary the rigidity of the implant 100 and 200, as well as the flexibility and mobility.

Pyramid-shaped serrations 203, which serve to engage the flexible space holder with the adjacent tissue to firmly anchor the space holder, are provided on end plates 226 and 225. Lid 226 also has engagement openings 229, so that end plate 226 can be screwed onto tube-like body 201.

The embodiments described above and shown herein are illustrative and not restrictive. The scope of the invention is indicated by the claims, including all equivalents, rather than by the foregoing description and attached drawings. The invention may be embodied in other specific forms without departing from the spirit and scope of the invention.

We claim:

1. A space holder for vertebrae and for intervertebral discs of at least one biocompatible material, the space holder comprising:
    a tube-like body having a longitudinal axis, the tube-like body comprising at least one rigid section having a tubular wall with a plurality of holes through the wall, and a flexible section adjacent to the rigid section, the flexible section having a helical recess separate from the plurality of holes;
    wherein the rigid section of the tube-like body further comprises an end portion configured to engage a body part, wherein the rigid and flexible sections are a continuous one-piece element;
    wherein the tubular wall of the rigid section defines an interior cavity radially inward from tubular wall, and each of the plurality of holes extending radially through the tubular wall to the interior cavity.

2. The space holder according to claim 1, wherein the biocompatible material is selected from the group comprising titanium, titanium alloys and plastics.

3. The space holder according to claim 1, wherein the recess is a groove-like recess formed in the wall of said tube-like body.

4. The space holder according to claim 3, wherein the recess is an open aperture in the wall of said tube-like body.

5. The space holder according to claim 1, wherein two recesses are formed in the tube-like body of said space holder.

6. The space holder according to claim 5, wherein said two recesses are groove-like recesses.

7. The space holder according to claim 5, wherein said two recesses are intertwined.

8. The space holder according to claim 1, wherein said space holder is compressible and extendable along a longitudinal axis of the tube-like body, bendable relative to the longitudinal axis, and torsionable about the longitudinal axis.

9. The space holder according to claim 1, wherein the end portion comprises projections.

10. The space holder according to claim 9, wherein said projections comprise serrations for engagement with adjacent body parts.

11. The space holder according to claim 10, wherein said projections are triangular.

12. The space holder according to claim 10, wherein said projections are trapezoidal.

13. The space holder according to claim 1, wherein the tube-like body is elastically extendable or compressible by about 0.5 to about 20% in the longitudinal direction.

14. The space holder according to claim 13, wherein the tube-like body is elastically extendable or compressible by about 1 to about 15% in the longitudinal direction.

15. The space holder according to claim 1, wherein the tube-like body is elastically bendable about a radial axis.

16. The space holder according to claim 15, wherein the end portion can pivot by about 0.5 to about 10° from a longitudinal axis of the tube-like body.

17. The space holder according to claim 16, wherein the end portion can pivot about 1 to about 6° from the longitudinal axis of the tube-like body.

18. The space holder according to claim 1, wherein said tube-like body is torsionable about a longitudinal axis, wherein the end portion is torsionable by about 0.5 to about 2.5°.

19. The space holder of claim 1, wherein the end portion has serrations around a circumference of the tubular wall, the serrations being configured to engage the body part.

20. The space holder of claim 1, wherein the plurality of holes are formed by intersecting bars of the rigid section around a circumference of the tubular wall.

21. The space holder of claim 20, wherein the intersecting bars form serrations to engage the body part.

22. The space holder of claim 21, wherein the serrations have a trapezoidal shape and are separated by triangular recesses around the circumference of the tubular wall.

23. The space holder of claim 1, wherein the plurality of holes comprises a row of diamond-shaped openings extending continuously around the circumference of the tubular wall.

24. A space holder for vertebrae and for intervertebral discs of at least one biocompatible material, the space holder comprising:
    a tube-like body comprising at least one rigid section having a tubular wall with a plurality of holes through the wall configured for growth of tissue, and a flexible section adjacent to the rigid section, the flexible section having at least one recess having a different shape than the plurality of holes and being separate from the plurality of holes;
    wherein the rigid section of the tube-like body further comprises an end portion configured to engage a body part;
    wherein the end portion has serrations around a circumference of the tubular wall for engagement with the body part;
    wherein the entire space holder is a monolithic body.

25. The space holder according to claim 24, wherein the at least one recess is a helical recess.

26. A space holder for vertebrae and for intervertebral discs of at least one biocompatible material, the space holder comprising:
    a tube-like body having a longitudinal axis, the tube-like body comprising at least one rigid section having a tubular wall with a plurality of holes through the wall, and a flexible section adjacent to the rigid section, the flexible section having a helical recess separate from the plurality of holes;
    wherein the rigid section of the tube-like body further comprising an end portion configured to engage a body part;
    wherein the tubular wall of the rigid section defines an interior cavity radially inward from the tubular wall, and each of the plurality of holes extending radially through the tubular wall to the interior cavity;
    wherein the end portion comprises projections to engage a body part; and,
    wherein the entire tube-like body including the at least one rigid section, the flexible section and the projections is a monolithic body.

* * * * *

UNITED STATES PATENT AND TRADEMARK OFFICE
CERTIFICATE OF CORRECTION

| | | |
|---|---|---|
| PATENT NO. | : 8,771,357 B2 | Page 1 of 1 |
| APPLICATION NO. | : 11/121888 | |
| DATED | : July 8, 2014 | |
| INVENTOR(S) | : Lutz Biedermann et al. | |

It is certified that error appears in the above-identified patent and that said Letters Patent is hereby corrected as shown below:

On the Title Page

(57) Abstract     Delete

"The present invention refers to a flexible space holder for temporary or permanent introdution into a human or animal body of at least one biocompatible, rigid material having a tube-like body (1), with one or more flexible areas being formed by material recesses mare provided for."

Insert

-- A flexible space holder made of at least one biocompatible, rigid material having a tube-like body, with one or more flexible areas is described. The flexible space holder can be temporarily or permanently inserted into a human or animal. Furthermore, the flexible space holder can be surrounded by an elastomeric sleeve. Alternatively, an elastic core can be inserted into the center of the flexible space holder. --

Signed and Sealed this
Twenty-ninth Day of March, 2016

Michelle K. Lee
*Director of the United States Patent and Trademark Office*